United States Patent [19]

Lynch et al.

[11] Patent Number: 4,940,520

[45] Date of Patent: Jul. 10, 1990

[54] PROCESS FOR THE PREPARATION OF 4-ACYLOXYAZETIDIN-2-ONE BY SINGLET OXYGEN OXIDATION

[75] Inventors: Joseph E. Lynch, Plainfield, N.J.; William L. Laswell, Perkasie, Pa.; Ralph P. Volante, East Windsor; Ichiro Shinkai, Westfield, both of N.J.

[73] Assignee: Merck & Co., Inc., Rahway, N.J.

[21] Appl. No.: 369,155

[22] Filed: Jun. 21, 1989

[51] Int. Cl.$^5$ .................... B01J 19/08; C07D 205/02; C07D 205/06

[52] U.S. Cl. .......................... 204/157.71; 204/157.93; 540/357; 540/200

[58] Field of Search ...................... 204/157.93, 157.71; 540/357, 400

[56] References Cited

U.S. PATENT DOCUMENTS

| | | | |
|---|---|---|---|
| 3,953,499 | 4/1976 | Pike et al. | 562/503 |
| 4,190,579 | 2/1980 | Wasserman | 540/362 |
| 4,260,618 | 4/1981 | Christensen | 424/263 |
| 4,315,998 | 2/1982 | Neckers | 525/332.2 |
| 4,791,207 | 12/1988 | Salzmann et al. | 548/110 |
| 4,849,076 | 7/1989 | Neckers | 204/157.93 |

FOREIGN PATENT DOCUMENTS 0167155 8/1986 European Pat. Off. .

J6 1243-079-A 1/1985 Japan .

OTHER PUBLICATIONS

Stuart L. Schreiber et al., Tetrahedron Ltrs, vol. 24, No. 23, pp. 2363-2366, 1983.

Bruce H. Lipshutz, Chem Rev. 1986, 795-819.

Maria Altamura, et al., Syn Comm., 18(16&17), 2129-2133 (1988).

Klaus Gollnick, et al. Tetrahedron vol. 41, No. 11, pp. 2057 to 2068, 1985.

Masao Shiozaki, et al., Tetrahedron vol. 40, No. 10, pp. 1795 to 1802, 1984.

Paul J. Reider, et al., Tetrahedron Lts, vol. 23, No. 22, pp. 2293-2296, 1982.

Curt Wentrup et al., J. Am. Chem. Soc. 1980, 102, 6161-6163.

Gunda I. Georg, et al. Tetrahedron Ltrs, vol. 26, No. 33, pp. 3903-3906, 1985.

Gunda I. Georg, et al., J. Am. Chem. Soc. 1987, 109, 1129-1136.

*Primary Examiner*—John F. Niebling
*Assistant Examiner*—Ben C. Hsing
*Attorney, Agent, or Firm*—J. W. Harbour; H. J. Pfeiffer

[57] ABSTRACT

The 4-acyloxyazetidin-2-ones, which are intermediates in the production of carbapenems and penems, are produced from 4-furanylazetidin-2-ones by singlet oxygen oxidation.

16 Claims, No Drawings

PROCESS FOR THE PREPARATION OF 4-ACYLOXYAZETIDIN-2-ONE BY SINGLET OXYGEN OXIDATION

The present invention relates to the preparation of 4-acyloxyazetidin-2-ones. More particularly, the present invention relates to the preparation of the above compounds through a 4-furan-2-ylazetidin-2-one intermediate.

BACKGROUND OF THE INVENTION

Carbapenems and penems are well known antibiotics for treating a broad range of gram-negative and gram-positive bacterial infections.

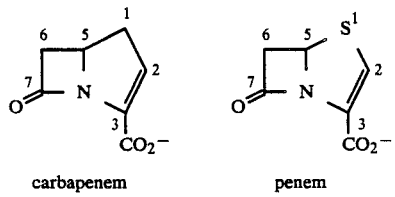

carbapenem    penem

Methods and intermediates for the manufacture of carbapenems and penems and thus matters of scientific and commercial importance.

One method for the production of carbapenems is described in GB No. 2,162,840, Cainelli, et al. As described therein, certain carbapenems are produced from 4-acetoxyazetidin-2-one intermediates.

These intermediates are inturn produced in a multi-step synthesis from 4-alkenylazetidin-2-one intermediates of the formula:

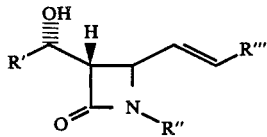

The starting materials to produce the 4-alkenylazetidin-2-one intermediates are:

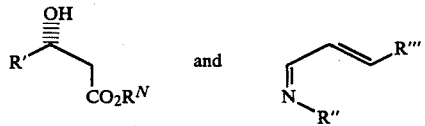

Thus, carbapenems may be produced through two principal intermediates from readily made or available starting materials. However, methods having fewer reaction steps to obtain the intermediates and improved yields are desirable.

Another method for the production of carbapenems is described in EPO No. 0167155, Kan, et al. Again certain carbapenems are produced from 4-acetoxyazetidin-2-one intermediates. In this case however, these intermediates are in turn produced from 4-triorganosiloxyazetidin-2-one intermediates of the formula:

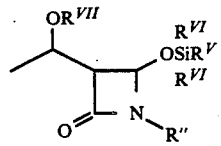

The starting materials to produce the 4-triorganosiloxyazetidin-2-one intermediates are:

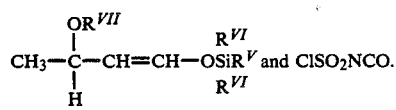

Thus, again, carbapenem may be produced through two principle intermediates from readily made or available starting materials. However, methods having fewer reactions steps to obtain the intermediates as well as methods using less hazardous starting materials then $ClSO_2NCO$ are desired.

A method for the production of penems is disclosed in Christensen, et al., U.S. Pat. No. 4,260,618 from 4-acetoxyazetidin-2-one intermediates. Herein, it is recommended that these intermediates be produced by cleaving penicillin which is produced by fermentation.

It is an object of the present invention to produce 4-acyloxyazetidin-2-one intermediates useful in the production of carbapenems.

It is a further object of the present invention to produce 4-acyloxyazetidin-2-one intermediates from starting materials which are easily handled on account of their low levels of toxicity.

It is yet another object of the present invention to simplify the reactions required and improve the reaction yields in the production of 4-acyloxyazetidin-2-one intermediates.

It is still another object of the present invention to develop a method for the production of 4-acyloxyazetidin-2-one intermediates where an organic group is employed to protect the carbon in the 4-position of the azetidin-2-one and which subsequently may be converted to the 4-acyloxy substitution without replacement.

BRIEF DESCRIPTION OF THE INVENTION

Briefly, there is provided by the present invention a method for the production of 4-acyloxyazetidin-2-ones comprising the steps of:

(a) contacting with singlet oxygen to react at temperatures below about 0° C. in organic solvent a compound of the formula (I):

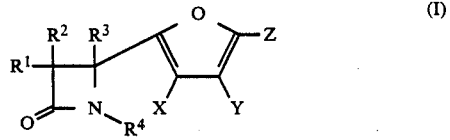

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is selected from the group consisting of hydrogen and a protecting group for nitrogen; and X, Y and Z are independently selected from the group consisting of hydrogen, halogen, $C_{1-10}$ alkyl, $C_6$ or $C_{10}$ aryl, substituted $C_6$ or $C_{10}$ aryl, $C_{1-10}$ alkoxy, and $C_6$ or $C_{10}$ aryloxy; and (b) warming the solution sufficiently to rearrange the reaction product of step (a) to the desired 4-acyloxyazetidin-2-one.

DETAILED DESCRIPTION OF THE INVENTION

Herein, $R^1$ and $R^2$ represent those hydrogen, alkyl, and substituted alkyl substituents useful as 6-position substitution on carbapenems or carbapenams. $R^1$ and $R^2$ include, for example, hydrogen, methyl, ethyl, propyl, isopropyl, butyl, isobutyl, $HO-CH_2-$, $CH_3CH(OH)-$, $(CH_3)_2C(OH)-$, $(CH_2)_2C(OH)-$, $CH_3CH_2CH(OH)-$, $CH_3CH_2CH_2CH(OH)-$, $CH_3CH_2CH(CH_3)(OH)-$, $CH_3CH(CH_3)CH(OH)-$, $CF_3CH(OH)-$, $CHF_2CH(OH)-$, $FCH_2CH(OH)-$, $CH_3CHF-$, $F_2CH-$, $F_3C-$, $CH_3CF_2-$, etc.

In preferred embodiments, either $R^1$ or $R^2$ is hydrogen and, in a more preferred embodiment, $R^2$ is beta-hydrogen and $R^1$ is any of the above, excepting hydrogen, in an alpha orientation. Most preferably, $R^1$ is an alpha oriented 1-hydroxyethyl and $R^2$ is a beta oriented hydrogen.

The protected hydroxy is known in the antibiotic art and refers to a hydroxyl group protected by a suitable protecting radical rendering it inactive during chemical reaction. Of course the identity of this protecting radical will depend on the particular chemical reaction from which the hydroxyl group is being protected. A preferred protecting radical useful herein in the production of the desired 4-acyloxy-azetidin-2-one is dimethyl-t-butylsilyl (TBDMS). This protecting radical may suitable for subsequent reactions of the desired compound or may require replacement depending on the scheme selected to produce penen or carbapenem. Further protecting groups which might be employed include trimethylsilyl, benzyl, p-nitrobenzyl, p-nitrobenzyloxycarbonyl, diphenyl-t-butylsilyl, isopropyldimethylsilyl, phenyl, methyl, etc. Other protecting radicals for hydroxyl groups are known in the art (see T. W. Greene, *Protective Groups in Organic Synthesis*, John Wiley & Sons, Inc., 1981).

$R^3$ may be selected from hydrogen, methyl, ethyl, propyl, etc. Preferably, $R^3$ is hydrogen and has a beta orientation.

As stated above, $R^4$ may be hydrogen or a protecting radical for nitrogen. Suitable protecting radicals for nitrogen include dimethyl-t-butylsilyl, trimethylsilyl, diphenyl-t-butylsilyl, triphenylsilyl, p-nitrobenzylcarbonyl, benzyl substituted benzyl, f-methoxy phenyl, etc. As above with the protecting radical for the hydroxyl group, the identity of any protecting radical and whether a protecting radical is at all necessary will depend on the chemical reactions from which the nitrogen group is being protected. For example, herein, the 4-furanylazetidin-2-one is produced by a suggested reaction between a furanyl substituted imine and the derivative of a carboxy compound. In this reaction, the nitrogen of the imine requires a protecting radical such as benzyl. The benzyl may be added to the nitrogen by well known reactions and subsequently replaced with another protecting group or with hydrogen as desired. It is a unique advantage of certain processes to produce 4-acyloxyazetidin-2-one taught herein from 4-furanylazetidin-2-one that no protecting radical is necessary for the nitrogen. Thus, it is preferred that the 4-furanyl azetidin-2-one of formula (1) have no protecting groups. Protecting radicals for nitrogen groups are well known in the art (See also, T. W. Greene, *Protective Groups In Organic Synthesis*, John Wiley & Sons, Inc., 1981).

Suitable X, Y and Z are independently selected from any of hydrogen, methyl, ethyl, propyl, t-butyl, n-butyl, phenyl, p-chlorophenyl, hydroxy, methoxy, ethoxy, phenoxy, etc. Preferably, at least Z is hydrogen. More preferably, X, Y and Z are hydrogen. The principle consideration of selecting X, Y and Z is that they not interfere with the processes taught herein.

Flow sheets A and B depict a suggested synthesis for the starting material described in formula (I). Flow Sheet A depicts the manufacture of an imine. This imine of Flow Sheet A is reacted with a carboxyl derivative in Flow Sheet B to produce the 4-furan-2-yl-azetidin-2-one starting material.

Referring to Flow Sheet A, an available or readily produced furfural 1 is condensed with an amine compound 2. In the case of such condensation, $R^4$ of compound 2 is not hydrogen. Preferably, of course, $R^4$ is a protecting radical for nitrogen and more preferably an organic aromatic protecting radical. Suitable as Compound 2 is benzylamine.

Referring to Flow Sheet B, compound 4 is a readily available or easily produced ester starting material having $R^1$ and $R^2$ substitution or precursors thereof. Suitable ester starting materials as compound 4 include methyl 3-hydroxypropanoate, methyl 3-hydroxypentanoate, methyl 3-hydroxy-4,4,4-trifluorobutanoate, methyl 3-fluorobutanoate, methyl 2-methyl-3-hydroxybutanoate, etc. Preferred is methyl 3-hydroxybutanoate. The nature of the ester group described as methyl is not critical and could be ethyl, propyl, etc.

As the first reaction step of Flow Sheet B, compound 4 is enolized by reaction with a base such as that prepared from n-butyllithium and diisopropylamine in tetrahydrofuran at about $-71°$ C. Subsequently and without isolation of the reaction product, the enolate is quenched by the addition of trimethylchlorosilane (TMS-Cl), again in tetrahydrofuran at about $-78°$ C., to produce a ketenesilylacetal, compound 5. In this reaction to produce compound 5, any unprotected hydroxy group on either $R^1$ or $R^2$ will be substituted with trimethylsilyl. This is a desirable result as a protecting group will later be necessary or any unprotected hydroxy of $R^1$ or $R^2$. If another type protecting group is desired, it should be added to the hydroxy of compound 4 prior to enolization. If another silyl protecting group is desired, then appropriate replacement should be made for trimethylchlorosilane in the reaction of quenching the enolate.

As the second reaction step of Flow Sheet B, the imine, compound 3, is added to the ketenesilylacetal, compound 5 in dichloromethane at about $-20°$ C. in the presence of trimethylsilyltrifluoromethanesulfonate (TMSOTf). The resultant compound 6 contains $R^1$ through $R^3$ functionality, $R^4$ functionality restricted to protecting radical for nitrogen and the necessary functionality to close the azetidin-2-one ring. At this point or later in Flow Sheet B, the protecting radical for nitrogen, $R^4$, may be converted to hydrogen or some other protecting radical to provide the full spectrum of $R^4$ substitution. For example, a benzyl protecting radical for nitrogen may be substituted with hydrogen through a hydrochloride by hydrogenation ($H_2$/Pd/C) in the presence of HCl and subsequent reaction with sodium hydroxide. Replacement of benzyl with other protecting radicals may be achieved by various methods known to persons skilled in the art.

As the third reaction of Flow Sheet B, compound 6 where $R^4$ is either hydrogen or protecting group for nitrogen according to the above, is saponified to remove the methyl ester and produced compound 7. The saponification is carried out in water, raising the pH to high levels with sodium hydroxide.

Finally, starting material 8 is produced by dehydrating compound 7 to close the azetidin-2-one ring. The dehydration is carried out in 2-propanol with $NaHCO_3$ and methane sulfonylchloride Mes-Cl. A preferred starting material 8 contains an $R^1$ with hydroxy substitution. This hydroxy substitution should be protected as appropriate from reaction conditions in which the starting material 8 is to be employed. The most preferred starting material 8 is shown in Example 6 as compound E9.

Flow Sheets C and D depict the process of the invention herein. Briefly, Flow Sheet C shows the singlet oxygen oxidation of 4-furanylazetidin-2-one to the desired 4-acyloxyazetidin-2-one. Flow Sheet D shows a variation of Flow Sheet C where a peroxide, ROOH, is present with the singlet oxygen.

Referring to Flow Sheet C, starting material 8 from Flow Sheet B is exposed to singlet oxygen which may be generated by contacting ground state oxygen with a photo-sensitizer which has been excited by irradiation with visible light at temperatures below about 0° C. The product of such exposure of starting material 8 is believed to be adducts 9 and 10 which have a fused peroxy ring on the 4-position furanyl. Without isolating adducts 9 and 10, a desired 4-acyloxy-azetidin-2-one 11 may be produced therefrom by simply warming to about room temperature i.e. about 0° C. to 50° C. The desired 4-acyloxyazetidin-2-one 11 may be easily converted to the most desired 4-acetoxy-azetidin-2-one 12 by transesterification using potassium acetate in water.

A number of methods are available for generating singlet oxygen, for example:

(1) Visible light exposure of ground-state molecular oxygen in the presence of a photosensitizer such as chlorophyl, hematoporphyin, Rose Bengal, eosin and the like, as described by A. Nickon and W. L. Mendelson, J. Am. Chem. Soc. 87, 3921 (1965) and K. Gollnick and G. O. Schenk, Pure and Applied Chem., 9,507 (1964), or as described in U.S. Pat. No. 3,281,415.

(2) Electrodeless discharge of gaseous oxygen, as described by E. J. Corey and W. C. Taylor, J. Am. Chem. Soc. 86, 3881 (1964).

(3) Use of hypochlorites and hydrogen peroxide. This method is described by C. S. Foote and S. Wexler, J. Am. Chem. Soc. 86, 3879 and 3881 (1964), and in U.S. Pat. No. 3,274,181.

(4) Use of the benzyl cyanide; hydrogen peroxide; base system, described by E. McKeown and W. A. Waters, Nature, 203, 1063 (1964).

(5) Use of hydrogen peroxide and oxalyl chloride, as described by E. A. Chandross, Tetrahedron Letters, 12,761 (1963), and Corey, cited above.

(6) Use of ozone and phosphines, phosphites, etc, as given by Q. E. Thompson, J. Am. Chem. Soc. 83,845 (1961) and Corey, cited above.

(7) By the reaction of hydrogen peroxide in aqueous solution with Fe (II), (III), or Ce (IV) ions, described by Stauff and Lohman, Z. physikal Chem., N. F., 40, 123 (1964) and (8) By pyrolysis of aromatic endoperoxides, such as anthracene or tryptycene endoperoxide. The 9,10-diarylanthracene endoperoxides are especially useful.

Of course, the method chosen should not produce by-products or have reagents that will undesirably react with the azetidinone intermediates or end-products. The preferred method generating singlet oxygen by visible light exposure of ground-state molecular oxygen in the presence of a photosensitizer.

In the preferred method, singlet oxygen is generated by contacting ground-state molecular oxygen with a suitable photosensitizer which is activated by irradiation with visible light in an appropriate organic solvent. The generation of the singlet oxygen and exposure of the starting material 8 to the singlet oxygen is carried out by bubbling oxygen through a solution containing photosensitizer, starting material 8, a light source and cooled to between −70° C. and 0° C. Suitable sensitizers are those organic compounds which have a large molar absorptivity in the visible part of the electromagnetic spectrum, a high quantum yield of triplet formation, a long triplet lifetime, a low tendency toward hydrogen abstraction and self-oxidation, and a triplet energy not far above the energy of singlet oxygen to permit efficient energy transfer to oxygen. Many common dyes meet these requirements adequately. Typical classes of dyes that can advantageously be used in the olefin oxidation process of this invention are the xanthenes (rose bengal, erythrosin, eosin, fluorescein), the thiasines (methylene blue), the porphyrins (chlorophyll a and b, hematoporphyrin), the porphins and the phthalocyanines and mixtures thereof. These and other dyes are disclosed in Denny, et al., in "Organic Reactions", vol. 20 (W. G. Dauben—editor-in-chief), published by John Wiley & Sons, pp. 133–136, incorporated herein by reference. A preferred dye sensitizer is methylene blue.

For optimum efficiency, the amount of photosensitizer should neither be very low nor very high. At very low concentrations the sensitizer may not absorb all the available useful light. At too high a concentration, it absorbs all the useful light within a short distance from its entrance to the solution and depletes oxygen in that region of the reaction vessel. Preferred amounts of sensitizer range from about 0.01% to about 2.5%, more preferably amounts range from about 0.05% to about 1.3%. Suitable organic solvents are preferably an alcohol, particularly the lower alkanols, e.g., methanol, ethanol, propanol, i-propanol, butanol, etc.

Any source of visible light is suitable for the activation of the sensitizer. However, for maximum efficiency, the source should strongly emit light of the wavelength corresponding with the absorptivity maximum of the sensitizer. Thus, a halogen lamp is suitable and a vapor discharge tube is particularly suitable for use herein.

Referring to Flow Sheet D, starting material 8 is exposed to singlet oxygen in the same manner as described in Flow Sheet C producing adducts 9 and 10. The difference herein with the exposure to singlet oxygen of Flow Sheet A is that there is also present in the solution a peroxide of the formula R'OOH which reacts with adducts 9 and 10 in situ to produce peroxide 13. Suitable R' are hydrogen or acyl of from 1 to 6 carbon atoms, for example, acetyl, propionyl, n-butyryl, isobutyryl, etc. Preferred R' are hydrogen and acetyl.

From peroxide 13 the reaction scheme to the desired 4-acyloxyazetidin-2-one differs depending on the nature of R'. Where R' is acyl, simply warming peroxide 13 from the sub-zero temperatures of exposure to singlet oxygen will rearrange and cleave the 4-furanyl substitution to 4-acyloxy. Where R' is hydrogen, peroxide 13 is treated with an organic acid anhydride in an organic solvent to about 0° C. to produce acylated compound 14. Suitable organic acid anhydrides include acetic acid anhydride, propionic acid anhydride, n-butyric acid anhydride, etc. Acylated compound 14 will rearrange and cleave the 4-furanyl substitution to 4-acyloxy upon warming from the 0° C. temperature of acylation.

Flow Sheet A

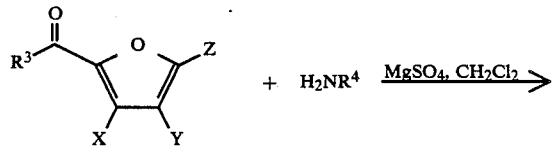

Flow Sheet B

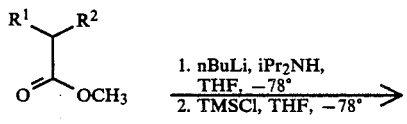

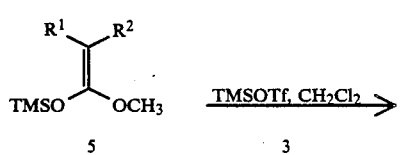

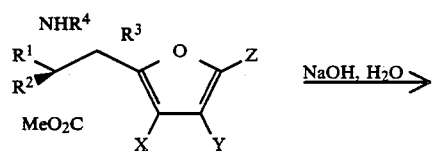

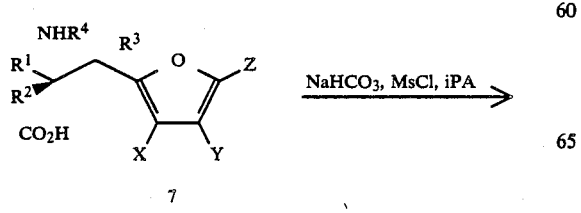

Flow Sheet B -continued

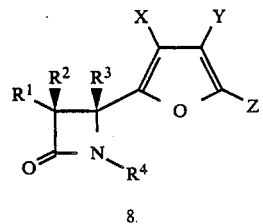

Flow Sheet C

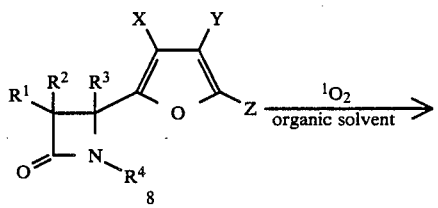

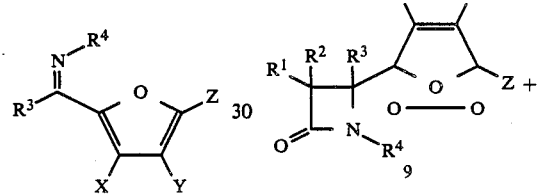

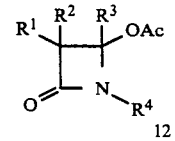

Flow Sheet D

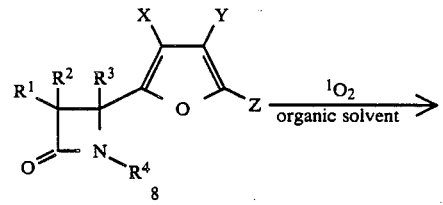

-continued
Flow Sheet D

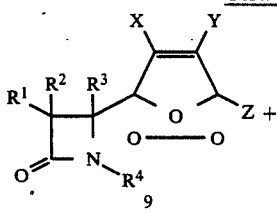
9

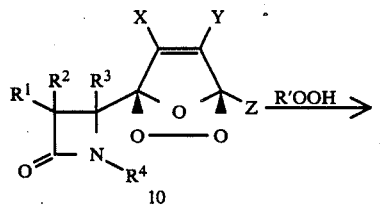
10

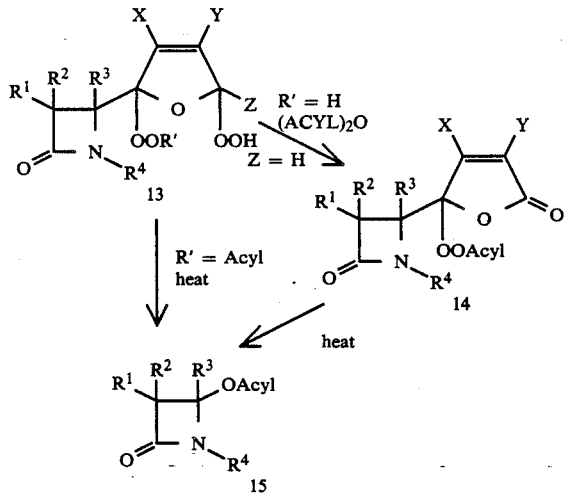

Any of compounds 11, 12 or 15 may be employed to make carbapenems or penems by well known methods. For example, 6-(1'-hydroxyethyl)-2-substituted-pen-2-em-3-carboxylic acid may be made from the above compounds as described in U.S. Pat. No. 4,260,618 hereby incorporated by reference. Therein, a 4-acyloxyazetidin-2-one is reacted with a substituted 1-thienoacetate derivative to provide a seco-lactam. Halogenation of the seco-lactam produces a compound which can be cyclized by treatment with a strong base to the penem. Further use of compounds 11, 12 and 15 to produce carbapenems are taught in Salzman, T.N., et al., J. Am. Chem. Soc., 1980, 102, 6161 and Reider, P.J., et al., Tetrahedron Lett., 1982, 23, 379.

The following examples are illustrative of the best mode of carrying out the instant invention as contemplated by us and should not be construed to be limitations on the spirit or scope of the instant invention.

EXAMPLE 1

(3R)-Z-1-Methoxy-1,3-bis-trimethylsilyloxy-1-butene

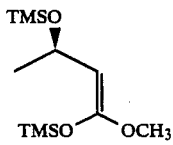
E2

1.54M nBuLi (237 mL, 0.365 mol) was added to diisopropylamine (41.15 g, 0.407 mol) in dry THF (740 ml) at −78° C. under $N_2$. (R) Methyl 3-hydroxybutanoate, E1, (20.00 g, 0.169 mol) in THF (340 mL) was added dropwise such that the temperature did not rise above −71° C. After a 30 minute age chlorotrimethylsilane (40.5 g, 0.373 mol) in THF (100 mL) was added so as to maintain the temperature below −71° C. The solution was stirred at −78° C. for 2 hours warmed to 0° C. and concentrated in vacuo. Hexane (500 mL) was added and the mixture concentrated again. A second portion of hexane (500 mL) was added and the mixture was filtered and concentrated to a pale yellow oil (40.76 g). Distillation gave silyl ketene, E2, as a clear colorless oil b.p. 75°–80° C./0.25 mm (30.32 g, 79%).

EXAMPLE 2

(2S,3R,1"R)-Methyl-2-(1'-N-benzylamino-1'-(furan-2"-yl))-3-hydroxybutyrate

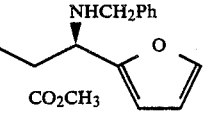
E5

Furfural E3 (4.98 g, 51.8 mmol) was added to benzylamine E4 (5.55 g, 51.8 mmol) in $CH_2Cl_2$ (25 mL). $MgSO_4$ (5 g) was added and the mixture was stirred for 2 hours, filtered and concentrated. The crude oil was redissolved in dry $CH_2Cl_2$ (60 mL) and concentrated repeatedly (2×) until the solution was dry (<10 mg $H_2O/L$). Trimethylsilyl trifluoromethanesulfonate (1.15 g, .5.18 mmol) was added to the imine above in $CH_2Cl_2$ (60 mL) at −20° C., after 5 minutes ketenesilylacetal, E2, (13.6 g, 51.8 mmol) was added and the solution aged for 18 hours. A second portion of ketenesilylacetal, E2, (3.6 g, 13.7 mmol) was added and the solution aged 16 hours. After warming to room temperature the solution was concentrated and redissolved in ethyl acetate (100 mL). The ethyl acetate solution was extracted with 2N HCl (50 mL); the aqueous solution was then treated with 5N $NH_4OH$ to give a pH>9 and was extracted with $CH_2Cl_2$ (50 mL). The $CH_2Cl_2$ solution was dried ($MgSO_4$) and concentrated to give amino ester, E5, as a yellow oil 13.78 g, 87.7%.

EXAMPLE 3

(2S,3R,1"R)-Methyl-2-(1'-amino-1'-(furan-2"-yl))-3-hydroxybutyrate Hydrochloride

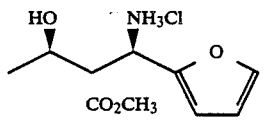
E6

12N HCl (0.48 mL, 5.76 mmol) and 10% Pd/C (170 mg) were added to the amino ester, E5, (1.75 g, 5.76 mmol) in methanol (17 mL). The mixture was hydrogenated at 1 psig $H_2$ at 25° C. until 98% of the starting material had been consumed (HPLC 1:1 $CH_3CN:H_2O$ (0.1% $H_3PO_4$), C8 column, 3 mL/min). The solution was filtered and concentrated to a white solid which was dissolved in 2-propanol (7 mL). Ethylether (30 mL) was then added dropwise with stirring to give hydrochloride, E6, as white needles which were collected on a filter, washed with 4:1 ether:2-propanol (2×5 mL) and dried in vacuo (1.21 g, 79.5%).

EXAMPLE 4

(2S,3R,1"R)-2-(1'-Amino-1'-(furan-2"-yl))-3-hydroxybutyric acid

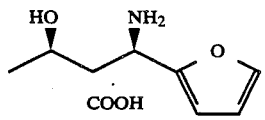

E7

The amino ester hydrochloride, E6, (55.69 g, 0.223 mol) was dissolved in H₂O (225 mL). 5N NaOH was added to pH=12.5; the pH was maintained at pH 12.5 with a pH controller for 18 hours. The solution was then acidified to pH 2 and loaded onto a column of Dowex 50 W×2 resin (700 mL). The column was washed with H₂O (1400 mL) then eluted with 1.5N NH₄OH. The fractions containing the amino acid were concentrated in vacuo to a white solid. 2-Propanol (400 mL) was added and the mixture was concentrated to dryness. The resulting solid was stirred in 2-propanol (400 mL) for 16 hours, collected on a filter, and then dried in vacuo to give amino acid, E7, as an off-white solid (40.99 g, 92.2%).

EXAMPLE 5

(1"R,3S,4R)-3-(1"-Hydroxyethyl)-4-(furan-2'-yl)azetidin-2-one

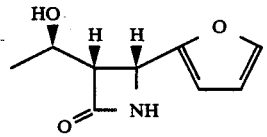

E8

NaHCO₃ (207.7 g, 2.47 mol) and then methanesulfonyl chloride (59.05 g, 0.51 mol) were added to dry 2-propanol (10.3 L). The amino acid E7 (40.99 g, 0.206 mol) was added and the mixture was stirred at 25° C. under N₂ for 39 hours. The mixture was concentrated, and the resulting solid triturated in ethyl acetate (2.5 L). The mixture was filtered and concentrated to a yellow oil (60 g). The oil was dissolved in ethyl acetate (100 mL), stirred with charcoal (3.5 g), filtered and concentrated to 120 ml. Hexane was added to the cloud point and the solution was seeded, hexane (total of 45 mL) was added dropwise. The mixture was stirred at ambient temperature for 1 hour, filtered and the solid was washed with 1:1 hexane:ethyl acetate (2×15 mL) and dried (13.17 g, 35%). The mother liquor was filtered through a short column of silica gel eluting first with 1:1 hexane:ethyl acetate (500 mL) then 1:2 hexane:ethyl acetate (500 mL); the fractions containing the azetidinone were concentrated to an oil that solidified on standing. The solid was broken-up and slurried in 1:1 hexane:ethyl acetate (30 mL), filtered, washed with the same solvent, (10 mL) and dried to give the desired azetidinone, E8, (11.31 g, 31%), total yield 66%.

EXAMPLE 6

(1"R,3S,4R)-2-S(1"'-t-Butyldimethylsilyloxyethyl)-4-(furan-2'-yl-azetidin-2-one

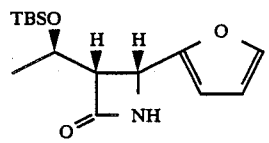

E9

Imidazole (5.63 g, 82.7 mmol) was added to 4-(furan-2-yl)-3-(1-hydroxyethyl)azetidin-2-one, E8, (10.00 g, 55.16 mmol) in dry DMF (25 mL). After cooling to 0° C., t-butyldimethylsilyl chloride (9.14 g, 60.67 mmol) was added, the cooling bath was removed and the solution was stirred at ambient temperature for 18 hours. Hexane:ethylacetate (1:1 75 mL) and water (50 mL) were added; the organic layer was washed with water (2×50 mL), dried (MgSO₄), and concentrated to give the silyloxy azetidinone, E9, as a yellow oil (16.08 g, 98.6%).

EXAMPLE 7

(1"R,3R,4S)-3-(1"'-t-Butyldimethylsilyloxy)-4-(3'-formyl-prop-2'-ene-1'-yl)-azetidin-2-one

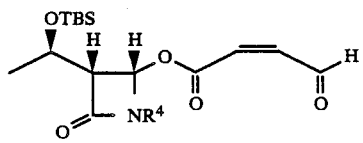

E10

Oxygen was bubbled through a solution of the furanylazetidinone, E9, (591 mg) and methylene blue chloride (5 mg) in acetone (10 mL) at −30° C. while irradiating with a 400 W halogen lamp for 2 hours. The solution was warmed to ambient temperature (22°–24° C.) and aged for 20 minutes. Concentration in vacuo and chromatography on silica gel gave the desired azetidinone, E10, as an oil 62 mg, 10%).

EXAMPLE 8

(1"R,3R,4R)-3-(1"'-t-Butyldimethylsilyoxyethyl)-4-acetoxyazetidin-2-one

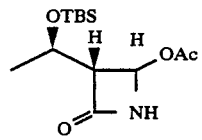

E11

Oxygen was bubbled through a solution of the furanylazetidinone, E9, (591 mg) and methylene blue chloride (5 mg) in acetone (10 mL) at −30° C. while irradiating with a 400 W halogen lamp for 2 hours. The solution was warmed to ambient temperature and after a 20 minute age, potassium acetate (anhydrous, 1 g) was added. The mixture was stirred for 5 hours and ether (20 ml) and water (10 mL) were added. The resulting emulsion was broken up by addition of saturated sodium chloride solution (5 mL), the organic layer was concentrated and chromatographed on silica gel (2:1 hexane:ethyl acetate) giving the acetoxy azetidinone, E11, as a white solid (134 mg, 23%).

EXAMPLE 9

(1″R,3R,4R)-3-(1″-t-butyldimethylsilyloxyethyl)-4-acetoxyazetidin-2-one E11 and (1″R, 3R, 4S)-3-(1″t-bytyldimethylsiyloxyethyl)-4-acetoxyazetidin-2-one E12.

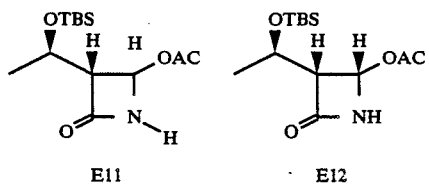

E11        E12

Oxygen was bubbled into a solution of the furanylazetidinone, E9, (295.6 mg, 1.00 mmol) and methylene blue (5 mg) in acetone (3 mL) and 30% $H_2O_2$ (1 mL) at −20° C. which was irradiated with a 400 W halogen lamp for 2 hours. The solution was warmed to 0° C., diluted with ether (20 mL), washed with water (3×10 mL), dried ($MgSO_4$), and concentrated to 5 mL. Methylene chloride (30 mL) was added and the solution was concentrated to 5 mL. The solution was cooled to 0° C., acetic anhydride (0.3 mL) and pyridine (0.28 mL) were added and the solution was allowed to stand at 0° C. for 16 hours. Hexane (7 mL) was added and the solution was washed with 2N HCl (2 mL) then 3% $NaHCO_3$ (5 mL), dried ($MgSO_4$), and concentrated to a brown foam (368.5 mg). Acetonitrile (3 mL) was added and the solution was heated at 50° C. for 4 hours, concentrated and chromatographed on silica gel (2:1 hexane:ethyl acetate) giving the acetoxyazetidinone, E11, (64 mg, 22%).

What is claimed is:

1. A method for the production of 4-acyloxyazetidin-2-ones comprising the steps of:
   (a) contacting with singlet oxygen to react at temperatures below about 0° C. in organic solvent a compound of the formula:

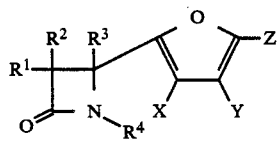

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is selected from the group consisting of hydrogen and a protecting group for nitrogen; and X, Y and Z are independently selected from the group consisting of hydrogen, halogen, $C_{1-10}$ alkyl, $C_6$ or $_{10}$ aryl, $C_{1-10}$ alkoxy, $C_6$ or $_{10}$ aryloxy; and
   (b) warming the solution sufficiently to rearrange the reaction product of step (a) to the corresponding 4-acyloxy azetidin-2-one.

2. The method of claim 1 wherein said contacting step additionally contains hydrogen peroxide and said contacting step (a) is followed by a step
   (i) contacting the reaction product of step (a) with an acylating agent 3. The method of claim 2 wherein said acylating agent is an organic acid anhydride.

4. The method of claim 3 wherein said organic acid anhydride is acetic acid anhydride.

5. The method of claim 1 wherein said contacting step additionally contains R'OOH wherein R' is acyl of from 1 to 6 carbon atoms.

6. The method of claim 5 wherein R' is acetyl.

7. The method of claim 1 wherein said singlet oxygen is generated by contacting ground state oxygen with a photosensitizer which has been excited by irradiation with visible light.

8. The method of claim 7 wherein said photo-sensitizer is methylene blue.

9. The method of claim 1 wherein said temperature is from about 0° C. to about −70° C.

10. The method of claim 1 wherein said solution of step (b) is warmed to about 0° C. to 50° C.

11. The method of claim 1 wherein step (b) is followed by a transesterification.

12. The method of claim 1 wherein either $R^1$ or $R^2$ is hydrogen.

13. The method of claim 1 wherein $R^2$ is beta-hydrogen and $R^1$ is other than hydrogen.

14. The method of claim 1 wherein $R^2$ is beta-hydrogen and $R^1$ is alpha oriented 1-hydroxyethyl.

15. The method of claim 1 wherein $R^4$ is hydrogen.

16. The method of claim 1 wherein X, Y and Z are hydrogen.

* * * * *